United States Patent [19]
Rios et al.

[11] Patent Number: 5,034,615
[45] Date of Patent: * Jul. 23, 1991

[54] PORTABLE FINGERPRINT DETECTION METHOD AND DEVICE

[75] Inventors: Arturo M. Rios, 2901 Fifth Ave. N., St. Petersburg, Fla. 33713; Michael Palermiti, Palm Bay, Fla.

[73] Assignee: Arturo M. Rios, Arecibo, Puerto Rico

[ * ] Notice: The portion of the term of this patent subsequent to Jan. 8, 2008 has been disclaimed.

[21] Appl. No.: 515,451

[22] Filed: Apr. 27, 1990

Related U.S. Application Data

[63] Continuation-in-part of Ser. No. 397,132, Aug. 22, 1989, Pat. No. 4,983,846.

[51] Int. Cl.$^5$ .............. G01J 1/58; G01J 1/00
[52] U.S. Cl. .............. 250/461.1; 250/458.1; 250/459.1; 250/341; 250/504 H
[58] Field of Search .............. 250/458.1, 459.1, 461.1, 250/461.2, 341

[56] References Cited

U.S. PATENT DOCUMENTS 4,773,097  9/1988  Suzaki et al. .............. 382/6
4,794,260  12/1988  Asano et al. .............. 250/458.1

Primary Examiner—Constantine Hannaher
Assistant Examiner—Edward J. Glick
Attorney, Agent, or Firm—Rogers & Killeen

[57] ABSTRACT

A device and method for detecting fluorescent evidence, including fingerprints. The device and method use a pair of matched filters, a source of noncoherent light, and a light intensifier to detect the wavelength-shifted luminescence from fluorescent substances. The light source and a first filter illuminate the substances with a light of predetermined band width. The second filter and the light intensifier detect and increase the luminance of the reflected light, shifted to a longer wavelength by luminescence from the florescent substances. The device may be hand-held and portable. The intensified light image may be displayed locally and/or may be transmitted to a remote receiver and displayed so that evidence may be detected remotely.

25 Claims, 3 Drawing Sheets

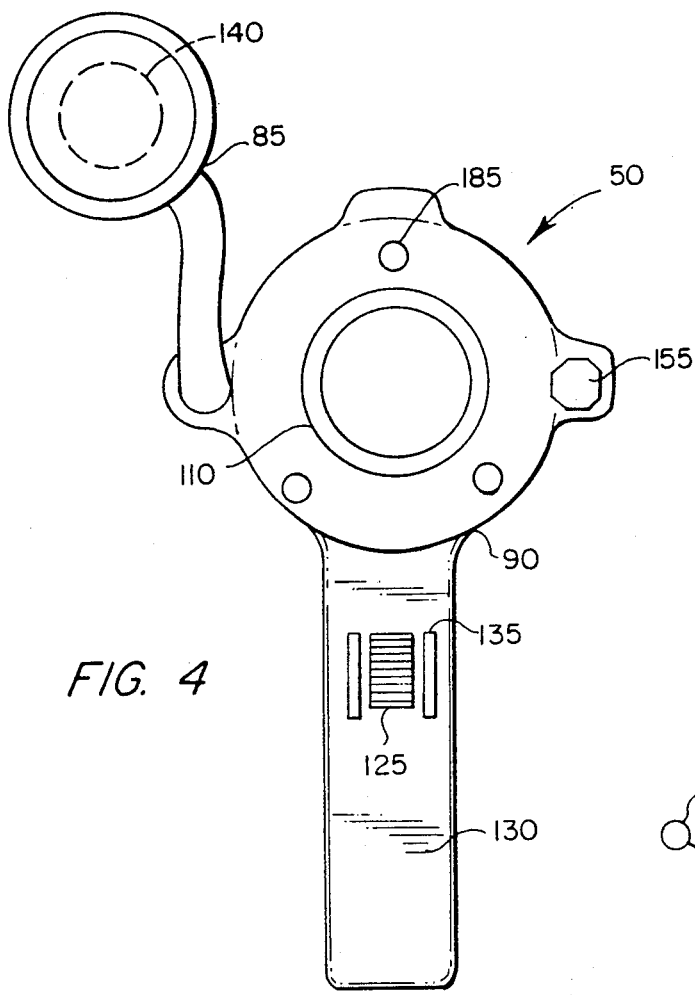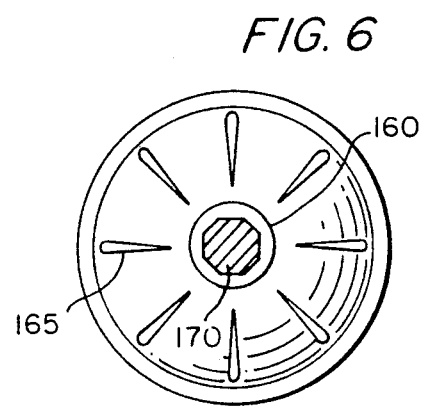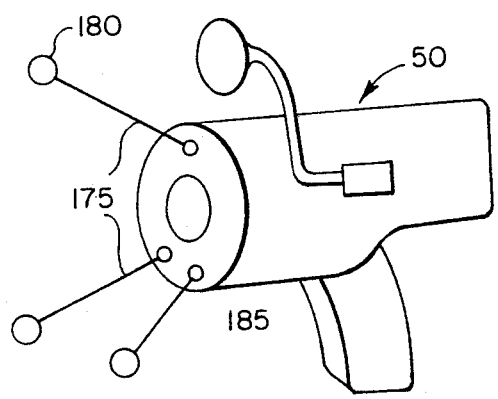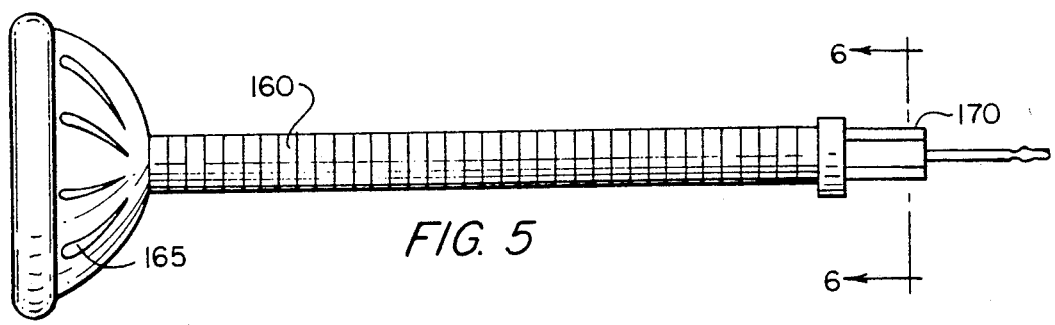

5,034,615

PORTABLE FINGERPRINT DETECTION METHOD AND DEVICE

This application is a continuation-in-part of U.S. application Ser. No. 397,132 filed Aug. 22, 1989.

BACKGROUND OF THE INVENTION

The present invention relates to devices and methods for detecting evidence at, for example, the scene of a crime. More particularly, it relates to devices and methods for detecting fluorescent substances and other materials or features which may be made fluorescent, such as fingerprints.

The detection of objects or features not normally visible to the human eye has long been recognized as a significant problem, especially in the field of law enforcement where detection of evidence is of critical importance. In this field the effort has focused on the improvement of the detection of fingerprints.

Devices and methods for detecting fingerprints frequently use lasers because of the laser's high detection rate. The laser excites fluorescent substances carried by the fingerprint making the fingerprint visible. The laser may excite fluorescent substances in the fingerprint residue itself, or fluorescent substances deposited on and carried by the fingerprint such as powders, dyes or chemical reagents. Such devices may also be used to detect fluorescent evidence other than fingerprints such as certain fibers and sweat. See, for example, U.S. Pat. Nos. 4,708,882 and 4,794,260 to Asano, et al.

Lasers, however, present new problems to the crime scene investigator. Their portability is extremely limited and they may be unwieldy in confined spaces because they require a large power supply which must be transported to the scene. They may also be unsafe to operate because the laser beam itself is hazardous and caution must be taken so that it does not reach the human eye either directly or by luminescence.

Fingerprints may, of course, be detected without lasers by using dusting powders, fuming and chemical reagents. Viewing may be enhanced by the use of ultraviolet light. See, for example, U.S. Pat. No. 4,504,408 to Morton. These techniques, however, generally have lower success rates than laser detection techniques. Old prints and prints on porous materials are particularly difficult to detect.

It is particularly desirable to record the image of the detected fluorescent evidence on videotape and/or to make hardcopy prints of the image. The equipment necessary to perform these functions, however, is not easily transported to the location of the evidence, especially if used in conjunction with the bulky laserdetectors. In some situations, it may be advantageous to transmit the image from the location of the evidence to remotely located recording and/or printing equipment. While systems for remotely displaying images are known for certain military applications, they have not been applied to evidence detection (see, for example, U.S. Pat. No. 4,786,966 to Hanson, et al.).

It is accordingly an object of the present invention to provide a novel device and method for detecting evidence, including fingerprints, that obviates the problems of the prior art and is portable and safe to use.

It is another object of the present invention to provide a novel device for detecting evidence, including fingerprints, without a laser, but with a relatively high degree of success.

It is yet another object of the present invention to provide a novel device for detecting evidence that illuminates fluorescent evidence with noncoherent light and detects the wavelength-shifted luminescence from the evidence with a light intensifier.

It is still another object of the present invention to provide a novel device for detecting fluorescent evidence without lasers that uses light filters having non-overlapping bandwidths for forming an image of the fluorescent evidence.

It is a further object of the present invention to provide a novel method for detecting fluorescent evidence without laser that includes illuminating the evidence with a specifically filtered light and detecting and intensifying the wavelengthshifted luminescence from the evidence.

It is yet a further object of the present invention to provide a novel method for detecting fingerprints using luminescence of noncoherent light filtered so that only the images of the fingerprints are received and intensified.

It is still a further object of the present invention to provide an apparatus which can be used by police and similar departments for plural purposes in the investigation of crime scenes and criminal activity.

It is also an object of the present invention to provide an evidence detection system that is portable, yet records images of the evidence and produces hard-copy prints of the images.

These and many other objects and advantages will be readily apparent to one skilled in the art to which the invention pertains from a perusal of the claims, the appended drawings, and the following detailed description of preferred embodiments.

THE DRAWINGS

FIG. 4 is a pictorial representation of a front view of the embodiment of the present invention illustrated in FIG. 3.

FIG. 5 is a pictorial representation of a side view of an embodiment of the light source in the present invention.

FIG. 6 is a pictorial representation of a cross section of the embodiment of the present invention illustrated in FIG. 5.

FIG. 7 is a pictorial representation of an embodiment of the present invention illustrating support legs.

DETAILED DESCRIPTION OF PREFERRED EMBODIMENTS

Figure 1:
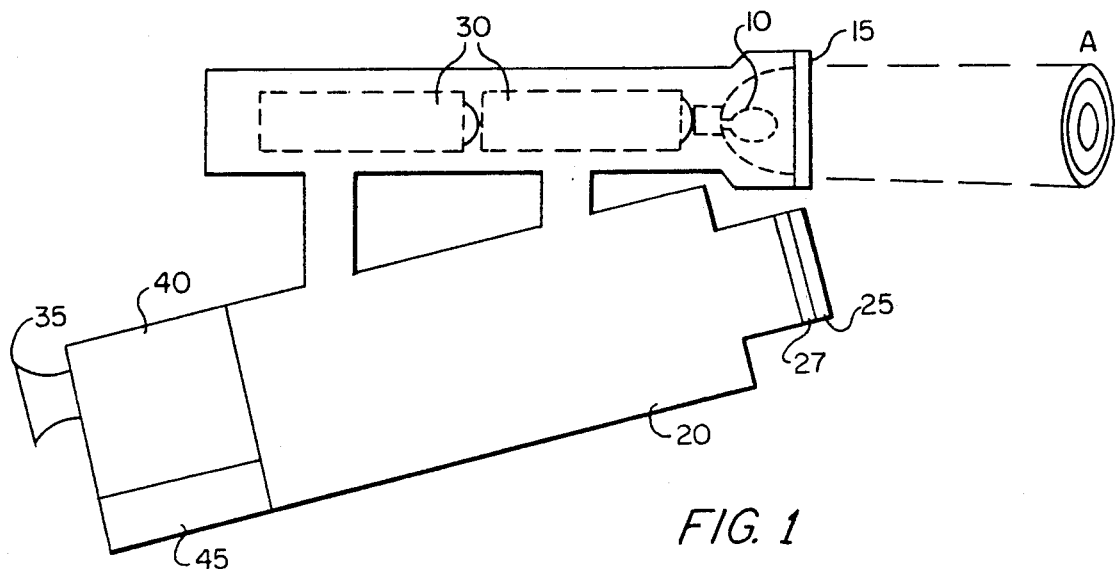
FIG. 1 is a pictorial representation of a side view of an embodiment of the detection device of the present invention.

With reference new to the figures where like elements have been given like numerical designations to enhance an understanding of the present invention, and particularly with reference to FIG. 1, the detection device of the present invention may include a source of noncoherent light 10 (lasers provide coherent light) for illuminating the evidence A, a first filter 15 for filtering light from the light source 10, a light intensifier 20 for receiving and intensifying light reflected from the evidence A, and a second filter 25 for filtering the reflected light before it is intensified.

In operation, the method and device of the present invention exploits the wavelength shift of light reflected from a fluorescent substance. As is well known, the wavelength of light is increased upon luminescence from a fluorescent substance (the light undergoes a wavelength shift in accordance with Stokes' Law). Thus, if a fluorescent substance is illuminated with light of a particular wavelength, the luminescence may be detected at a longer wavelength.

In the present invention, light from light source 10 is filtered by filter 15 to illuminate a fluorescent substance with light having a predetermined band of wavelengths, for example, 555 to 565 nanometers. When a fluorescent substance is so illuminated, the luminescence from the substance may be detected in a band of wavelengths about 10% longer (10% is the wavelength shift at this incident wavelength); 610 to 622 nanometers in this example. By providing a second filter 25 that filters out light outside the wavelength band of the reflected light, only the desired luminescence are detected. The filters 15 and 25 thereby cooperate to first illuminate and then enable detection of fluorescent substances.

To enhance detection of the luminescence, a light intensifier 20 may be provided to increase the luminance of the luminescence. The luminescence have been found to be particularly dim, even when the source is bright. The intensifier increases the luminance of the luminescence so that relatively high detection rates may be achieved.

To further enhance detection, the present invention may be operated when the fluorescent substances are shielded from all other light sources. By so doing, the intensifier does not receive light at the wavelength band of the second filter that may be reflected from objects other than those activated by the filtered light source.

The method of the present invention may also include the application of a fluorescent substance to evidence (e.g., fingerprint) so that its image may be more clearly seen. While any known application system is acceptable, dusting is preferred to enhance the portability of the present method and to reduce damage to the material bearing the fingerprints.

When a fine fluorescent dust is applied to a surface bearing a fresh fingerprint, the dust adheres more readily to the oil which forms the print than to the surrounding surface. The oil typically has been left in a pattern resembling the valleys between fingerprint ridges. Thus, the dust concentrates in a pattern resembling the fingerprint and the fingerprint fluoresces. If the fingerprint is not fresh or is dry, there is little or no oil on which the dust can adhere. However, in drying the oil typically turns into an amino acid which etches the surface at the submicron level. While such etching is often invisible to the naked eye, even if aided by conventional black fingerprint dusting powders, the fine dust of the fluorescing powder will be relatively more trapped by the etching traces and thereby reveal the ridge pattern of the of the fingerprint which originally was left on the surface.

With further reference now to FIG. 1, the light source 10 may be any source of noncoherent light, such as an incandescent lamp containing halogen or krypton with a tungsten filament. It is desirable that the source have a luminous intensity of about 100 lux. While a practical minimum intensity depends on the strength of the intensifier, it has been found that below about 25 lux the efficiency of the intensifier is reduced by the introduction of noise.

Light emitting diodes (LED) may be grouped and optically coupled to form a light source with a particular wavelength. LEDs, however, reduce the viewing area have lower luminous intensity.

The first filter 15 may be any known fine-cut filter that is capable of creating a wavelength band (the one-half bandpass) of between 5 and 15 nanometers, with about 10 nanometers preferred. The center wavelength is desirably in the range of 500 to 600 nanometers, with about 560±4.8 nanometers preferred. In the 500-600 nanometer band, the preferred wavelength has been found to produce the highest overall detection rate of fluorescing evidence (e.g., fingerprints, body fluids, hair) on a wide variety of surfaces, such as paper, plastic, metal, wood and glass. The term "filter" as used herein also includes the elements in an LED that create a light source of a particular wavelength.

The second filter 25 may be identical to the first filter 15, except that the wavelength band should be correspondingly 10% higher.

The wavelength bands of filters 15 and 25 should not be so large that they overlap. If the bands were to overlap, reflected light that has not been wavelength shifted by the fluorescent material may be received, degrading operation of the device. A separation of about 10 nanometers is acceptable, with about 20 nanometers preferred. Increased separation improves the signal-to-noise ratio throughout the system, thus improving image quality as measured by both spatial resolution and contrast.

Where evidence detection is by ultraviolet light, the center wavelength of the first filter is desirably in the range of a center 300 to 400 nanometers, with about 334 nanometers preferred. In this event, the center wavelength of the second filter may be about 20% higher; that is about 405 nanometers when the first filter operates at 334 nanometers. The wavelength shift caused by the fluorescent material is greater at shorter wavelengths.

Where the present invention is to operate in the infrared spectrum, the first filter may be an infrared filter with a long wave cutoff at about 1100 nanometers. In this event, the second filter may admit all wavelengths from about 400 to 1100 nanometers.

A lens 27 may be provided with the filter 25 to enhance the light-gathering power of the device. While a particular minimum power is not required, a power of f/2.0 or better (e.g., f/1.6) is preferred. The lens 27 may have a variable focal length and iris opening. Alternatively, or in addition, the filter may be in form of or integral with the lens.

The relatively broad wavelength band of the filters 15 and 25 (10 nanometers, as compared with 0.1 nanometers for lasers) increases the efficiency of the filters. For example, the first filter 15 may have an efficiency of 50% and the second filter 25, 90%. These relatively high efficiencies allow the use of a lower power intensifier 20. This is significant in the present invention because a low power intensifier has reduced energy requirements and increased portability.

The light intensifier 20 may be any known means for increasing the luminance of light it receives. While an intensifier capable of increasing luminance several thousand times is acceptable, an increase of about twenty thousand is preferred. Intensifier 20 may be, for example, a television system capable of detecting and intensifying low levels of light. A second generation microchannel plate is preferred because it provides low "blooming" (highly luminescent luminescence do not wash out weaker luminescence), high contrast and resolution, and is easily adapted for TV and photographic cameras.

The present invention may be completely portable. Batteries 30, such as common 1.5 volt dry cell batteries, may be provided to power the light source 10 and intensifier 20. Appropriate circuitry may be provided so that the device may operate from household current as well.

The images produced by the intensifier may be viewed through an eyepiece 35 that may be focused. The images may be reproduced with a camera 40, such as a photographic or television camera. A remote monitor may also be provided. A video recording system 45 may be included so that images may be replayed later.

Figure 2:
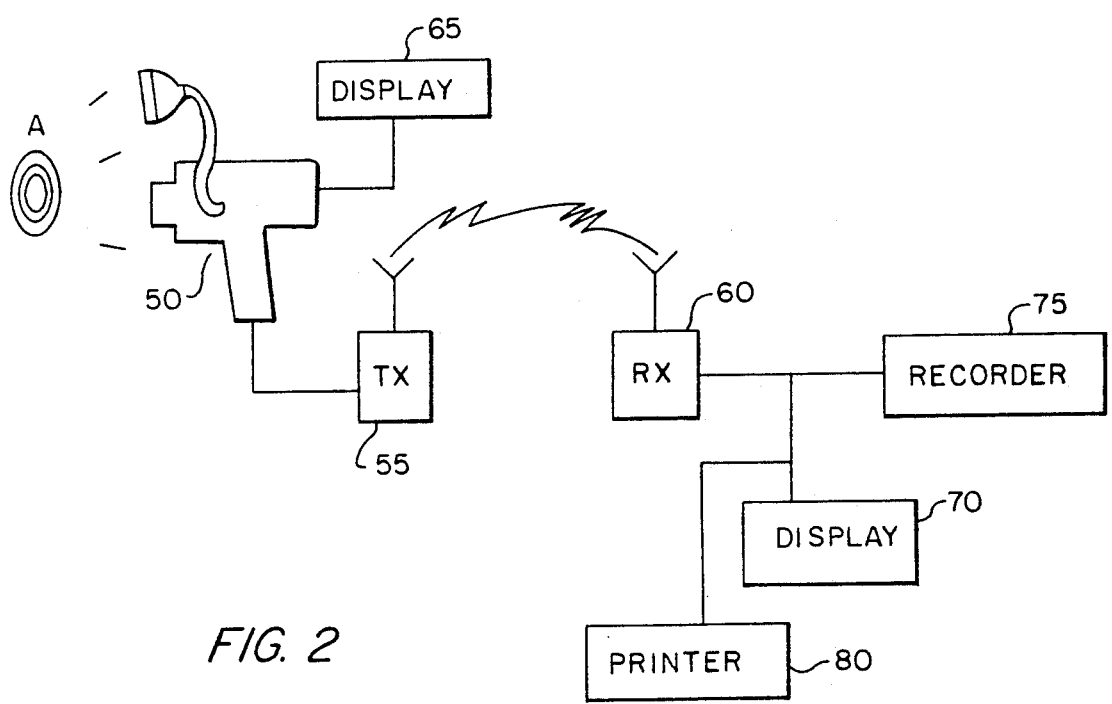
FIG. 2 is a schematic representation of a detection system of the present invention.

With reference now to FIG. 2, a system of the present invention for detecting evidence may include a handheld detector unit 50 for detecting and generating an image of the evidence A and a transmitter 55 for transmitting the image to a receiver 60 that may be remote from the evidence. Displays 65 and 70 for the image may be adapted to operate with the detector unit 50 and receiver 60, respectively. An appropriate recorder 75 and/or printer 80 may also be provided.

In operation, the detector unit 50 and transmitter 55 may be hand carried to the scene of the evidence where detector unit 50 may be used to detect the evidence and to generate an image in the form of a signal that may be transmitted by transmitter 55. A support facility, such as a car or truck located within range of the transmitter, may be provided for the receiver 60, display 70, recorder 75, printer 80 and associated equipment. Signals generated by detector unit 50 may thereby be viewed and saved without transporting the equipment for such tasks to the evidence. Display 65 may be used at the scene so that the operator of detector unit 50 may more easily detect and view the evidence.

Figure 3:
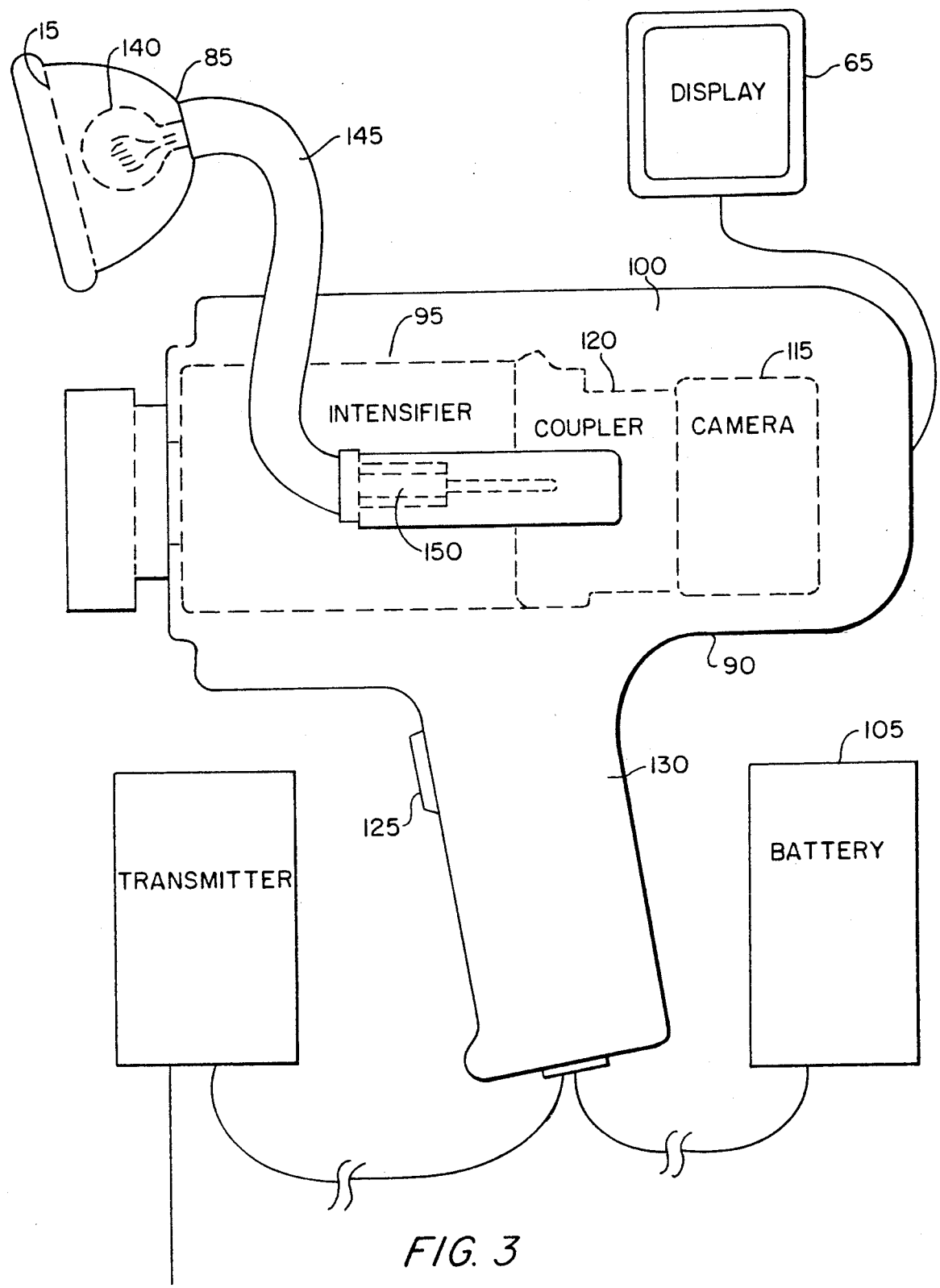
FIG. 3 is a partial pictorial and partial schematic representation of a side view of an embodiment of the present invention.

With reference to FIGS. 3 and 4, the detector unit 50 may include a source of noncoherent light 85 removably attached to a case 90 housing the intensifier 95 and image generator 100. Transmitter 55 and batteries 105 may be connected to unit 50 and carried by the operator of the unit 50 in a belt or harness (not shown). Display 65 may also be connected to unit 50 and may be carried by unit 50 or by the operator on a headpiece or harness (not shown).

A 25 millimeter f/1.4 television lens 110 may be removably attached to the case 90. The second filter 25 may be integrated with the lens 110 or removably attached thereto. The intensifier 95 may be a 25 millimeter micro-channel plate intensifier. The image generator 100 may include a camera 115, such as a charged couple device (CCD) image sensor, and an appropriate optical coupling system 120 for coupling the intensifier 95 to the camera 115. The image generator may operate in the NTSC RS 170 video format. This embodiment may provide a two inch diameter viewing area eight inches from the lens 110.

The case 90 may be impact-resistant and include a trigger 125 on a hand grip 130 for operating the detector unit 50. Trigger guards 135 may be provided.

The source of noncoherent light 85 may be movably positioned so that light at an appropriate incident angle and distance from the evidence may be provided. One or more sources of light 85 may be used, with two sources being preferred. As may be seen in FIGS. 3 and 4, the source of light 85 may be attached to the side of the case 90 and operated by the trigger 125 through appropriate circuitry.

Each source of light 85 may include a source of broadband light 140 mounted at one distal end of a flexible neck 145 and a first filter 15 carried by light source 140. A removably attachable plug 150 may be provided at the other distal end of the neck 145 for mating with a corresponding socket 155 in the case 90. In operation, the light source 85 may be replaced with a light source having a first filter with different filtering characteristics. Light source 85 (with first filter 15) and lens 110 (with second filter 25) may be removed and replaced at the same time to provide various filter combinations as desired by the operator to meet different detection requirements.

With reference now to FIGS. 5 and 6, the source of noncoherent light may include a flexible goose-neck 160 that is pliant, but retains its shape when moved. The broadband light source 140 may be housed in a unit with vents 165 for cooling. A male connector 170 for connecting the source 85 to the case 90 may have planar faces that correspond to planar faces in the socket 155 in the case. The use of planar faces, such as the octagonally shaped connectors shown in FIGS. 4 and 6, permits the source of light 85 to be held at various angles without rotational slippage. This feature is desirable when the light source 85 must be positioned and held at a particular angle to illuminate hard-to-reach evidence.

As may be seen in FIG. 7, the detector unit 50 may also include one or more stabilizing legs 175 for holding unit 50 a predetermined distance from the evidence. The length of the legs 175 may be set so that image focus may be maintained. Rollers 180 and the like may be provided at the distal ends of the legs so that unit 50 may be slideably moved over the location of the evidence while maintaining image focus. The legs may be removably attached to the case 90 on the front thereof in receptacles 185 located so as not to interfere with the sources of light 85.

While preferred embodiments of the present invention have been described, it is understood that the embodiments described are illustrative only and that the scope of the invention is to be defined solely by the appended claims when accorded a full range of equivalence, many variations and modifications naturally occurring to those skilled in the art from the perusal thereof.

We claim:

1. A system for detecting fluorescent evidence, including fingerprints, without a laser by illuminating evidence which is fluorescent, and receiving the luminescence from the fluorescent evidence that has been wavelength-shifted in accordance with Stokes' Law, comprising:

a detector unit comprising,
 (a) a noncoherent light source for illuminating fluorescent evidence;
 (b) a first filter for filtering light from said light source, said first filter having a first predetermined center wavelength;
 (c) a light intensifier for receiving luminescence from the illuminated evidence and for intensifying the luminescence at least several thousand times;
 (d) a second filter for filtering light received at said light intensifier, said second filter having a second predetermined center wavelength, said second center wavelength being separated from said first center wavelength by approximately the Stokes' Law wavelength shift, said first and second filters having one-half bandpasses much less than the Stokes' Law wavelength shift, and (e) image generation means for providing a signal representative of the intensified luminescence;

a receiver and a display not connected to said detector unit for displaying the intensified luminescence remotely; and transmission means for transmitting said signal from said detector unit to said receiver.

2. The system as defined in claim 1 wherein said image generation means comprises a charged couple device image sensor, and an optical coupling system.

3. The system as defined in claim 2 wherein said image generation means further comprises means for operating in a NTSC RS 170 video format.

4. The system as defined in claim 1 further comprising means for recording the signal received at said receiver.

5. The system as defined in claim 1 wherein said noncoherent light source comprises a source of broadband light and means for movably positioning said source of broadband light with respect to said detector unit.

6. The system as defined in claim 5 further comprising means for removably attaching said noncoherent light source from said detector unit.

7. The system as defined in claim 6 wherein said means for removably attaching comprises a male connector affixed to said means for movably positioning and having planar faces, and a female connector in said detector unit and having corresponding planar faces so that said light source is removably attached to said detector unit when said male and female connectors are mated.

8. The system as defined in claim 5 wherein said source of broadband light carries said first filter.

9. The system as defined in claim 8 wherein said first center wavelength is between 500 and 600 nanometers.

10. The system as defined in claim 8 wherein said first center wavelength is between 300 and 400 nanometers.

11. The system as defined in claim 8 wherein said first filter is an infrared filter with an 1100 nanometer wavelength cutoff.

12. The system as defined in claim 1 further comprising a local display carried by and connected to said detector unit so that fluorescent evidence may be detected locally.

13. The system as defined in claim 1 further comprising a battery for operating said detector unit.

14. The system as defined in claim 1 further comprising at least one support leg removably attached to said detector unit for providing a predetermined distance between said second filter and the evidence.

15. The system as defined in claim 14 wherein said support leg comprises roller means at the distal end thereof for slideably moving said detector unit.

16. A device for detecting fluorescent evidence comprising:

(a) light means for illuminating the fluorescent evidence with light of a first predetermined wavelength band, said light means comprising,
  (i) a source of broadband noncoherent light,
  (ii) filter means for filtering light from said source of light so that light of said first wavelength band is emitted by said light means,
  (iii) means for movably positioning said source of light so that the evidence may be illuminated thereby;

(b) detection means for intensifying light of a second predetermined wavelength band luminescing from the fluorescent evidence and for generating an image thereof so that the evidence may be detected; and (c) attachment means for removably attaching said light means to said detection means.

17. The system as defined in claim 16 wherein said attachment means comprises a male connector affixed to a distal end of said means for movably positioning and a female connector in said detection means so that said light means is removably attached to said detection means when said male and female connectors are mated.

18. The system as defined in claim 17 said male and female connectors each have plural corresponding planar faces for preventing rotation of said light source means when said male and female connectors are mated.

19. The system as defined in claim 16 wherein said means for movably positioning comprises a flexible tubular neck having said source of light affixed to one distal end thereof.

20. The system as defined in claim 16; wherein said first wavelength band is 300 to 400 nanometers.

21. The system as defined in claim 16 wherein said first wavelength band is 500 to 600 nanometers.

22. The system as defined in claim 16 wherein said first wavelength band is infrared with an 1100 nanometer wavelength cutoff.

23. The system as defined in claim 22 said second wavelength band is 400 to 1100 nanometers.

24. A method for detecting fluorescent evidence, including fingerprints, without a laser, comprising the steps of:

(a) illuminating the fluorescent evidence with a broadband noncoherent light source so that at least parts thereof luminesce;

(b) filtering light from said light source so that light reaching the evidence has a first predetermined center wavelength;

(c) filtering the luminescence from the evidence at a second predetermined center wavelength;

(d) intensifying the filtered luminescence at least several thousand times; and (e) creating a signal representative of the intensified luminescence;

(f) displaying said signal so that the fluorescent evidence may be detected.

25. The method as defined in claim 24 further comprising the steps of:

(g) transmitting said signal to a receiver remote from the evidence; and (h) displaying the transmitted signal so that the evidence may be detected remotely from the evidence.

* * * * *